(12) United States Patent
Zhang

(10) Patent No.: US 7,736,054 B2
(45) Date of Patent: Jun. 15, 2010

(54) X-RAY DETECTING DEVICE AND X-RAY IMAGING APPARATUS

(75) Inventor: Jinglei Zhang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/437,269

(22) Filed: May 7, 2009

(65) Prior Publication Data

US 2009/0279671 A1 Nov. 12, 2009

(30) Foreign Application Priority Data

May 9, 2008 (CN) .................. 2008 1 0099125

(51) Int. Cl.
*H01J 31/50* (2006.01)
(52) U.S. Cl. .................. 378/189; 378/167; 378/197
(58) Field of Classification Search .................. 378/37, 378/98.8, 102, 167, 177, 178, 181, 189, 196–197
See application file for complete search history.

(56) References Cited

U.S. PATENT DOCUMENTS

| | | | |
|---|---|---|---|
| 3,984,696 A | 10/1976 | Collica et al. | |
| 4,233,516 A * | 11/1980 | Trepte | 378/181 |
| 5,305,365 A * | 4/1994 | Coe | 378/37 |
| 5,388,141 A | 2/1995 | Hove | |
| 5,533,089 A | 7/1996 | Mulhern | |
| 5,572,567 A | 11/1996 | Khutoryansky et al. | |
| 6,075,256 A | 6/2000 | Kaifu et al. | |
| 6,142,667 A | 11/2000 | Pattee | |
| 6,450,684 B2 | 9/2002 | Kobayashi | |
| 6,683,935 B2 | 1/2004 | Moore | |
| 6,979,123 B2 | 12/2005 | Barta et al. | |
| 7,380,985 B2 * | 6/2008 | Zhang | 378/189 |

FOREIGN PATENT DOCUMENTS

JP 2004-298473 10/2004

* cited by examiner

*Primary Examiner*—Hoon Song
(74) *Attorney, Agent, or Firm*—Armstrong Teasdale LLP

(57) ABSTRACT

An X-ray detecting device comprises a support mechanism for supporting a detector housing pivotably about a horizontal shaft parallel to an X-ray incidence surface, a shaft connected at one end to the detector housing and having an opposite end adapted to perform a rectilinear motion to induce a pivotal motion of the detector housing, a drive mechanism having a drive end connected to the opposite end of the shaft, the drive mechanism inducing the rectilinear motion of the opposite end of the shaft in a mutually connected state of the drive end and the opposite end of the shaft, a switching mechanism for between connection and non-connection of the opposite end of the drive shaft and the drive end, a brake mechanism for inhibiting the pivotal motion of the detector housing, and brake operating means for switching between operation and non-operation of the brake mechanism.

20 Claims, 10 Drawing Sheets

X-RAY DETECTING DEVICE AND X-RAY IMAGING APPARATUS

CROSS REFERENCE TO RELATED APPLICATIONS

This application claims the benefit of Chinese Patent Application No. 200810099125.9 filed May 9, 2008, which is hereby incorporated by reference in its entirety.

BACKGROUND OF THE INVENTION

The embodiments described herein relate to an X-ray detecting device and an X-ray imaging apparatus. Particularly, the embodiments described herein are concerned with an X-ray detecting device including a detector housing having an X-ray incidence surface whose direction is changeable, as well as an X-ray imaging apparatus equipped with such an X-ray detecting device.

In an X-ray imaging apparatus, X-ray is radiated from an X-ray irradiator to a subject and transmitted X-ray is detected by an X-ray detector to form a radioscopic image. A certain X-ray imaging apparatus uses an X-ray stand. In the X-ray stand, a detector housing which incorporates an X-ray detector is supported by a vertical column. The X-ray stand is constructed such that the height of the detector housing and the direction of an X-ray incidence surface can be adjusted in accordance with a region to be radiographed (see, for example, Japanese Unexamined Patent Publication No. 2004-298473).

BRIEF DESCRIPTION OF THE INVENTION

Adjustment of the direction of an X-ray incidence surface in a detector housing is performed using the power of a motor for example, but it is required that the direction be also adjustable manually for taking an appropriate measure in the event of motor failure or emergency.

Accordingly, embodiments of the present invention provide an X-ray detecting device in which the direction of an X-ray incidence surface of a detector housing can be adjusted by both power and hand, as well as an X-ray imaging apparatus equipped with such an X-ray detecting device.

A first aspect of the present invention provides an X-ray detecting device, with the direction of an X-ray incidence surface of a detector housing of the X-ray detecting device being changeable, comprising: a support mechanism for supporting the detector housing pivotably about a horizontal shaft parallel to the incidence surface; a shaft connected at one end thereof to the detector housing and having an opposite end adapted to perform a rectilinear motion to induce a pivotal motion of the detector housing; a drive mechanism having a drive end connected directly or indirectly to the opposite end of the shaft, the drive mechanism inducing the rectilinear motion of the opposite end of the shaft in a mutually connected state of the drive end and the opposite end of the shaft; a switching mechanism for switching from one to the other between connection and non-connection of the opposite end of the shaft and the drive end; a brake mechanism for inhibiting the pivotal motion of the detector housing; and a brake operating means for switching from one to the other between operation and non-operation of the brake mechanism.

A second aspect of the present invention, in combination with the above first aspect, provides an X-ray detecting device further comprising a shaft support joined to the opposite end of the shaft and a restriction mechanism for restricting a moving direction of the shaft support, wherein the drive end is connected to the shaft support.

A third aspect of the present invention, in combination with the above first aspect, provides an X-ray detecting device wherein the support mechanism supports a back surface of the detector housing by being apart from the horizontal shaft disposed on the back side of the detector housing.

A fourth aspect of the present invention, in combination with the above third aspect, provides an X-ray detecting device wherein the support mechanism has a pair of parallel support arms spaced from each other in the direction of the horizontal shaft.

A fifth aspect of the present invention, in combination with the above fourth aspect, provides an X-ray detecting device wherein the support arms are engaged with the horizontal shaft at respective ends on the side opposite to the detector housing.

A sixth aspect of the present invention, in combination with the above second aspect, provides an X-ray detecting device, wherein the restriction mechanism comprises: a rectilinear rail; and a slider adapted to move on the rail while carrying the shaft support thereon.

A seventh aspect of the present invention, in combination with the above second aspect, provides an X-ray detecting device, wherein the drive mechanism comprises: a motor; a drive shaft connected at a drive end thereof to the shaft support and adapted to be driven by the motor to thereby reciprocate in a rectilinear direction; and a second support mechanism for supporting the motor and the drive shaft pivotably about a second horizontal shaft parallel to the horizontal shaft on the side opposite to the drive end, causing a force induced by a turning moment to act on the contact portion between the drive end and the shaft support.

An eighth aspect of the present invention, in combination with the above seventh aspect, provides an X-ray detecting device wherein the switching mechanism has a lever for lifting the drive mechanism to pull the drive end apart from the shaft support.

A ninth aspect of the present invention, in combination with the above first aspect, provides an X-ray detecting device wherein the brake mechanism comprises: a second shaft connected at one end thereof through a pin parallel to the horizontal shaft to a position spaced apart from the horizontal shaft on a back side of the detector housing; and a brake for inhibiting movement of the second shaft.

A tenth aspect of the present invention, in combination with the above ninth aspect, provides an X-ray detecting device wherein the brake is an electromagnetic brake.

An eleventh aspect of the present invention provides an X-ray imaging apparatus comprising an X-ray detecting device, with the direction of an X-ray incidence surface of a detector housing of the X-ray detecting device being changeable, and an X-ray irradiation device, the X-ray detecting device comprising: a support mechanism for supporting the detector housing pivotably about a horizontal shaft parallel to the X-ray incidence surface; a shaft connected at one end thereof to the detector housing and having an opposite end adapted to perform a rectilinear motion to induce a pivotal motion of the detector housing; a drive mechanism having a drive end connected directly or indirectly to the opposite end of the shaft, the drive mechanism inducing the rectilinear motion of the opposite end of the shaft in a mutually connected state of the drive end and the opposite end of the shaft; a switching mechanism for switching from one to the other between connection and non-connection of the opposite end of the shaft and the drive end; a brake mechanism for inhibiting the pivotal motion of the detector housing; and brake operating means for switching from one to the other between operation and non-operation of the brake mechanism.

A twelfth aspect of the present invention, in combination with the above eleventh aspect, provides an X-ray imaging apparatus further comprising: a shaft support joined to the opposite end of the shaft; and a restriction mechanism for restricting a moving direction of the shaft support, wherein the drive end is connected to the shaft support.

A thirteenth aspect of the present invention, in combination with the above eleventh aspect, provides an X-ray imaging apparatus wherein the support mechanism supports a back surface of the detector housing by being apart from the horizontal shaft disposed on the back surface side of the detector housing.

A fourteenth aspect of the present invention, in combination with the above thirteenth aspect, provides an X-ray imaging apparatus wherein the support mechanism has a pair of parallel support arms spaced from each other in the direction of the horizontal shaft.

A fifteenth aspect of the present invention, in combination with the above fourteenth aspect, provides an X-ray imaging apparatus wherein the support arms are engaged with the horizontal shaft at respective ends on the side opposite to the detector housing.

A sixteenth aspect of the present invention, in combination with the above twelfth aspect, provides an X-ray imaging apparatus, wherein the restriction mechanism comprises: a rectilinear rail; and a slider adapted to move on the rail while carrying the shaft support thereon.

A seventeenth aspect of the present invention, in combination with the above twelfth aspect, provides an X-ray imaging apparatus, wherein the drive mechanism comprises: a motor; a drive shaft connected at a drive end thereof to the shaft support and adapted to be driven by the motor to thereby reciprocate in a rectilinear direction; and a second support mechanism for supporting the motor and the drive shaft pivotably about a second horizontal shaft parallel to the horizontal shaft on the side opposite to the drive end, causing a force induced by a turning moment to act on the contact portion between the drive end and the shaft support.

An eighteenth aspect of the present invention, in combination with the above seventeenth aspect, provides an X-ray imaging apparatus wherein the switching mechanism has a lever for lifting the drive mechanism to pull the drive end apart from the shaft support.

A nineteenth aspect of the present invention, in combination with the above eleventh aspect, provides an X-ray imaging apparatus wherein the brake mechanism comprises: a second shaft connected at one end thereof through a pin parallel to the horizontal shaft to a position spaced apart from the horizontal shaft on a back side of the detector housing; and a brake for inhibiting movement of the second shaft.

A twentieth aspect of the present invention, in combination with the nineteenth aspect, provides an X-ray imaging apparatus wherein the brake is an electromagnetic brake.

In the embodiments described herein, the direction of a detector housing is changeable, and the X-ray detecting device comprises a support mechanism for supporting the detector housing pivotably about a horizontal shaft parallel to the X-ray incidence surface, a shaft connected at one end thereof to the detector housing and having an opposite end adapted to perform a rectilinear motion to induce a pivotal motion of the detector housing, a drive mechanism having a drive end connected directly or indirectly to the opposite end of the shaft, the drive mechanism inducing the rectilinear motion of the opposite end of the shaft in a mutually connected state of the drive end and the opposite end of the shaft, a switching mechanism for switching from one to the other between connection and non-connection of the opposite end of the shaft and the drive end, a brake mechanism for inhibiting the pivotal motion of the detector housing, and brake operating means for switching from one to the other between operation and non-operation of the brake mechanism. Consequently, it is possible to provide an X-ray detecting device including a detector housing having an X-ray incidence surface whose direction is changeable, as well as an X-ray imaging apparatus having such an X-ray detecting device.

The X-ray detecting device further comprises a shaft support joined to the opposite end of the shaft and a restriction mechanism for restricting a moving direction of the shaft support, and the drive end is connected to the shaft support.

Consequently, the direction of the X-ray incidence surface of the detector housing can be adjusted properly.

Since the support mechanism supports a back surface of the detector housing apart from the horizontal shaft disposed on the back surface side of the detector housing, the detector housing can be allowed to swing about the horizontal shaft.

Since the support mechanism has a pair of parallel support arms spaced from each other in the direction of the horizontal shaft, it is possible to support the detector housing stably.

Since the support arms are engaged with the horizontal shaft at respective ends on the side opposite to the detector housing, it is possible to utilize the length of each support arm.

Since the restriction mechanism comprises a rectilinear rail and a slider adapted to move on the rail while carrying the shaft support thereon, it is possible to restrict the moving direction properly.

The drive mechanism comprises a motor, a drive shaft connected at a drive end thereof to the shaft support and adapted to be driven by the motor and thereby reciprocate in a rectilinear direction, and a second support mechanism for supporting the motor and the drive shaft pivotably about a second horizontal shaft parallel to the horizontal shaft on the side opposite to the drive end, causing a force induced by a turning moment to act on the contact portion between the drive end and the shaft support. Consequently, the drive end can be brought into contact with the shaft support by utilizing the turning moment.

Since the switching mechanism has a lever for lifting the drive mechanism to pull the drive end apart from the shaft support, it is possible to perform switching between contact and non-contact easily.

The brake mechanism comprises a second shaft connected at one end thereof through a pin parallel to the horizontal shaft to a position spaced apart from the horizontal shaft on a back side of the detector housing and a brake for inhibiting movement of the second shaft. Consequently, it is possible to inhibit movement of the detector housing properly.

Since the brake is an electromagnetic brake, it is possible to control the brake electrically. In this case, by providing the brake operating means with a switch for the electromagnetic brake, it is possible to operate the brake easily.

DETAILED DESCRIPTION OF THE INVENTION

Embodiments of the invention will be described in detail with reference to the drawings. The present invention is not limited to the embodiments described herein. The construction of an exemplary X-ray imaging apparatus is shown schematically in FIG. 1.

Figure 1:
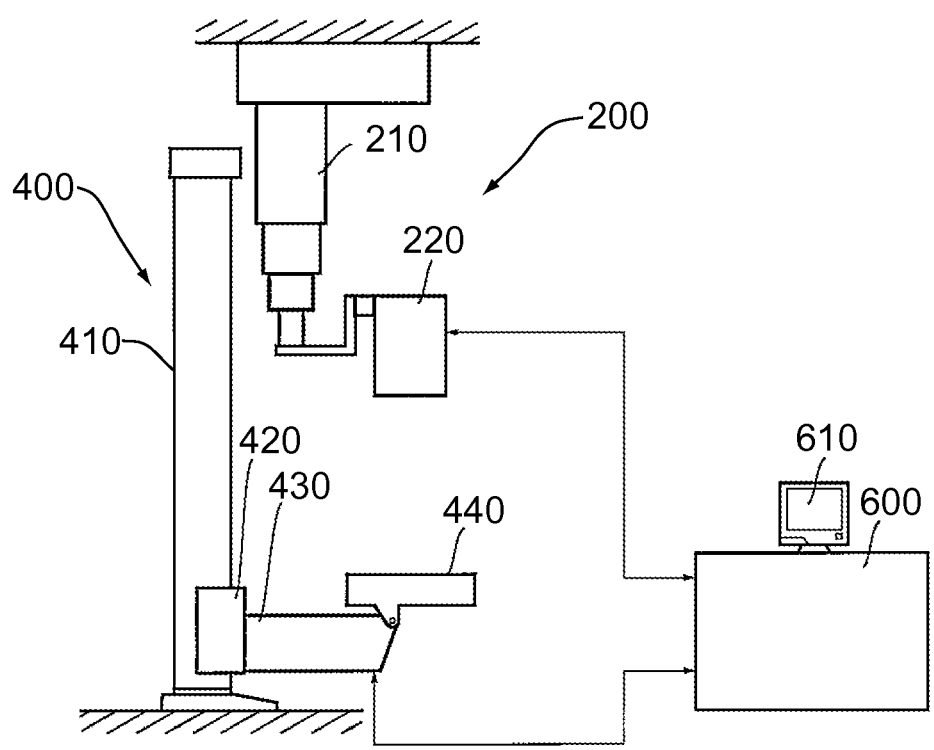
FIG. 1 is a view showing the construction of an exemplary X-ray imaging apparatus.

As shown in FIG. 1, this apparatus includes an X-ray irradiation device 200 and an X-ray detecting device 400. The X-ray irradiation device 200 is made up of a column 210 suspended from a ceiling and an X-ray irradiator 220 attached to a lower end of the column 210. The X-ray irradiator 220 can change its direction, thereby making it possible to change the X-ray irradiating direction. The column 210 which supports the X-ray irradiator 220 is capable of expansion and contraction in its longitudinal direction and is movable horizontally along the ceiling. The X-ray irradiation device 200 is an example of the X-ray irradiation device defined in the present invention.

In the X-ray detecting device 400, a carriage 420 is attached vertically movably to a column 410 which is erected upright on a floor, an arm 430 is attached to the carriage 420 horizontally, and a detector housing 440 is attached to a tip end portion of the arm 430. The X-ray detecting device 400 is a so-called wall stand type X-ray detecting device.

The X-ray detecting device 400 is an example of the best mode for carrying out the invention. With the construction of the X-ray detecting device 400, there is shown an example of the best mode for carrying out the invention with respect to the X-ray detecting device.

The detector housing 440 is a flat structure in the shape of a rectangular parallelepiped and incorporates an X-ray detecting panel. The detector housing 440 has an X-ray incidence surface whose inclination is adjustable so as to provide a horizontal or vertical state or any other desired angle in accordance with an incidence direction of X-ray. The detector housing 440 is an example of the detector housing defined in the present invention.

An X-ray detection signal is inputted to an operator console 600 from the detector housing 440. On the basis of the input signal from the detector housing 440, the operator console 600 reconstruct a radioscopic image of the subject and displays it on a display 610.

The operator console 600 controls both X-ray irradiation device 200 and X-ray detecting device 400. For the X-ray irradiation device 200, the operator console 600 controls horizontal and vertical positions and X-ray irradiating direction of the X-ray irradiator 220 and further controls X-ray intensity and irradiation timing. For the X-ray detecting device 400, the operator console 600 controls the height of the detector housing 440 so as to match the X-ray irradiator 220, and adjusts the angle of the detector housing 440, thereby controlling the direction of the X-ray incidence surface in conformity with the X-ray incidence direction.

A mechanism for controlling the direction of the X-ray incidence surface of the detector housing 440 in accordance with a control signal provided from the operator console 600 is provided in the interior of the arm 430. The following description is now provided about an angle adjusting mechanism for controlling the direction of the X-ray incidence surface.

Figure 2:
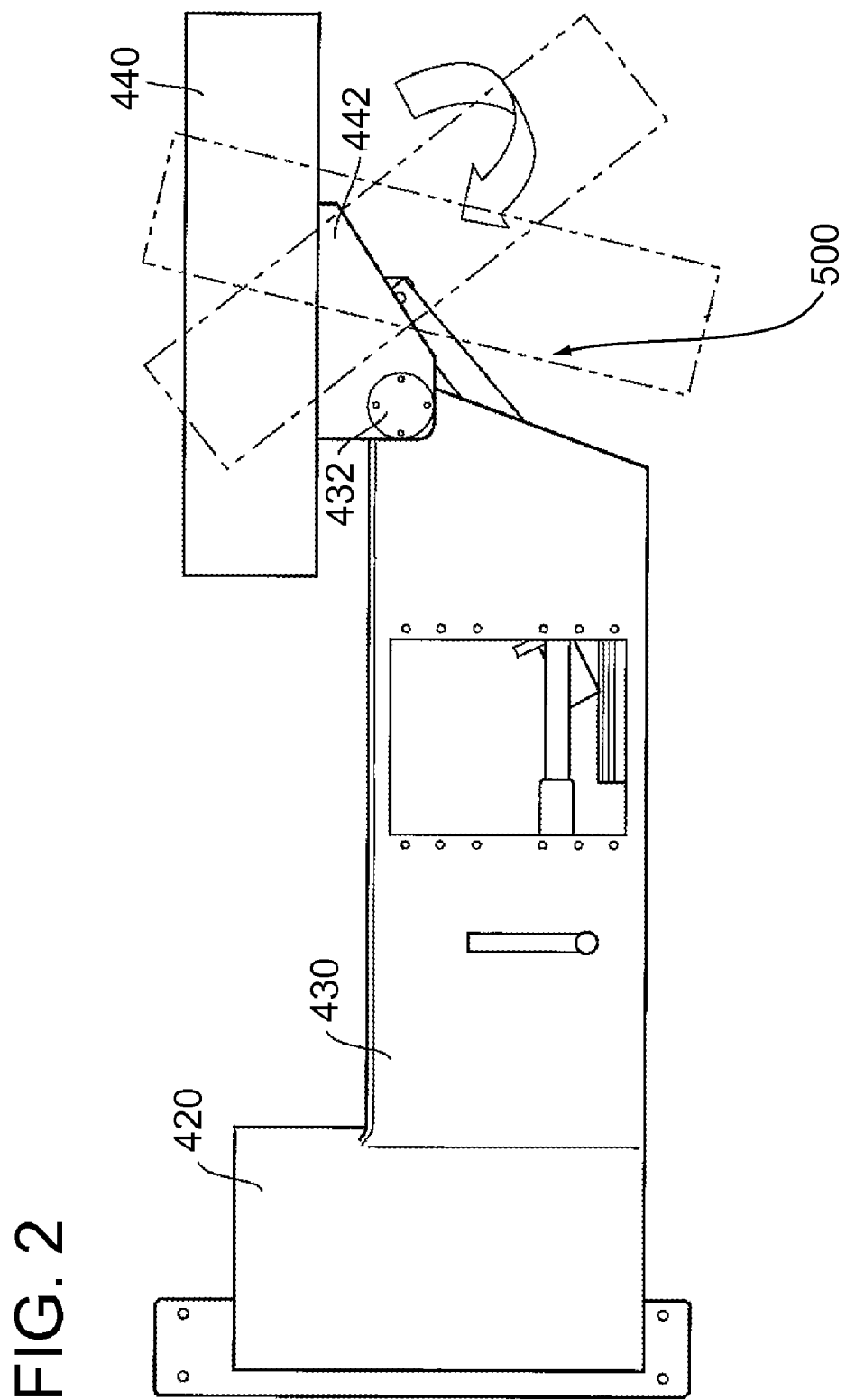
FIG. 2 is a view showing an appearance of an arm which incorporates an angle adjusting mechanism.

FIG. 2 shows an appearance of the arm 430 which incorporates the angle adjusting mechanism. As shown in FIG. 2, the arm 430 has a horizontal shaft 432 in an upper position of its tip and the detector housing 440 is attached to the horizontal shaft 432 pivotably through a bracket 442.

The bracket 442 is provided on a back side, namely, the side opposite to the X-ray incidence surface located on the surface side, of the detector housing 440. With the bracket 442, a predetermined distance from the horizontal shaft 432 up to the back surface of the detector housing 440 is ensured.

With this distance as a radius the detector housing 440 pivots and causes the angle of the X-ray incidence surface to change from 90° (horizontal) to −20° via 0° (vertical). The angle of the X-ray incidence surface will also be referred to hereinafter as the angle of the detector housing.

The angle adjustment of the detector housing 440 is performed by an angle adjusting mechanism 500 disposed within the arm 430. The angle adjusting mechanism 500 is constructed so as to also permit manual adjustment of the angle of the detector housing 440.

Figure 3:
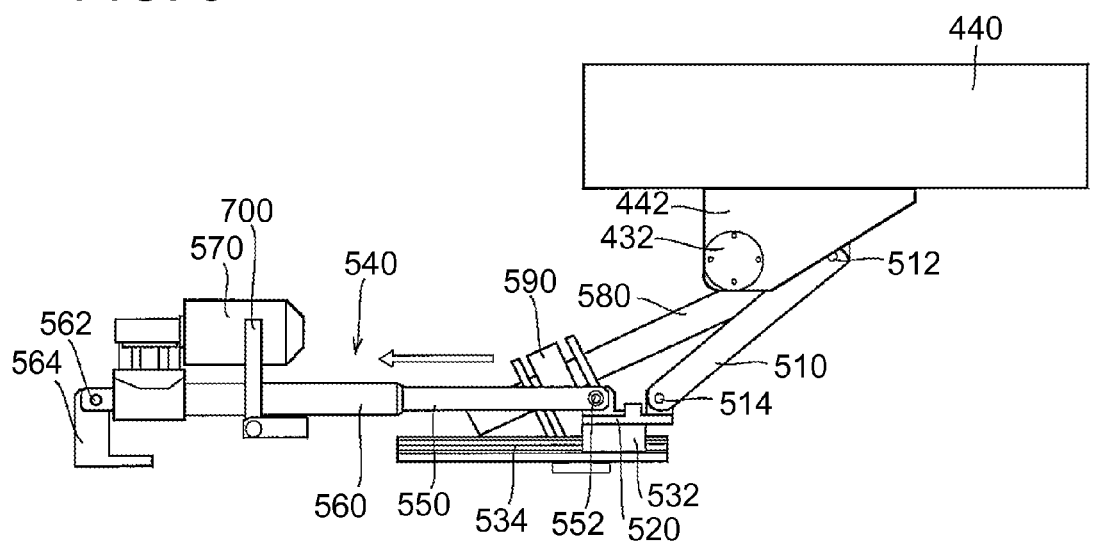
FIG. 3 is a view showing a constructional example of the angle adjusting mechanism.
Figure 4:
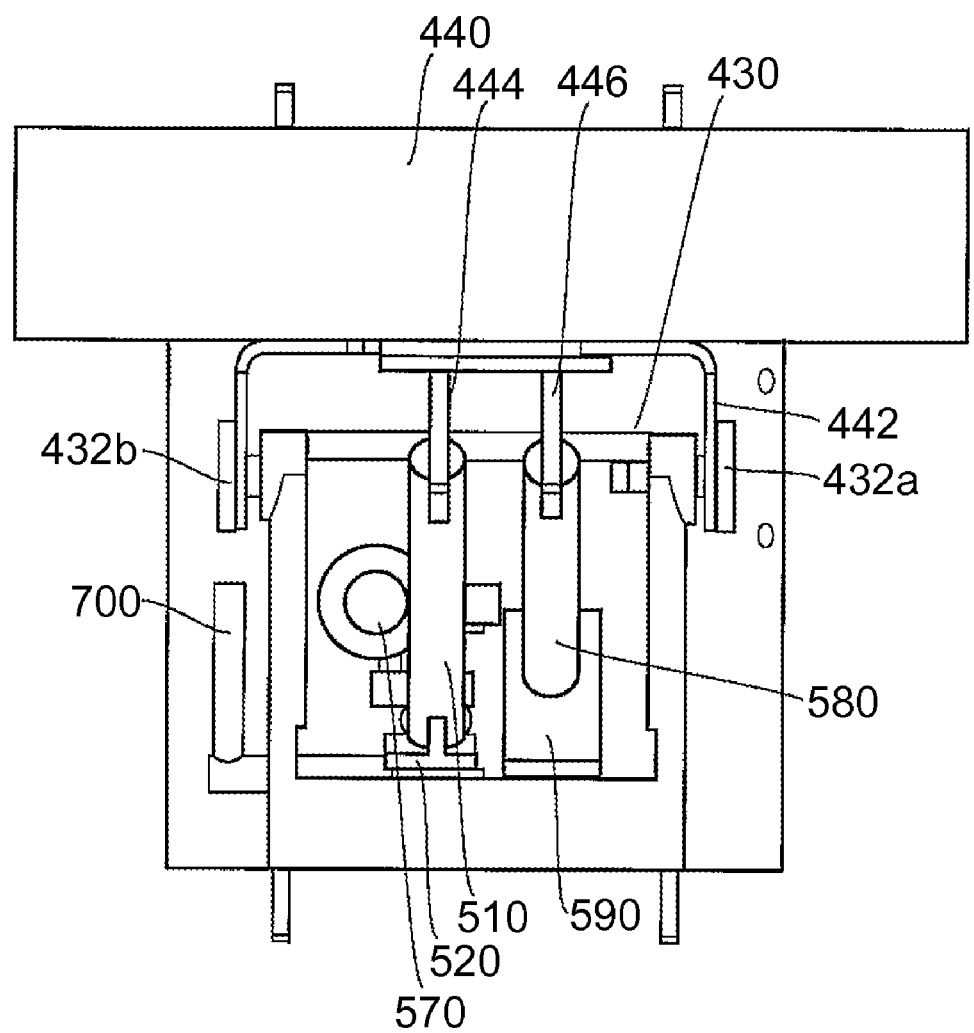
FIG. 4 is a view showing a constructional example of the angle adjusting mechanism.
Figure 5:
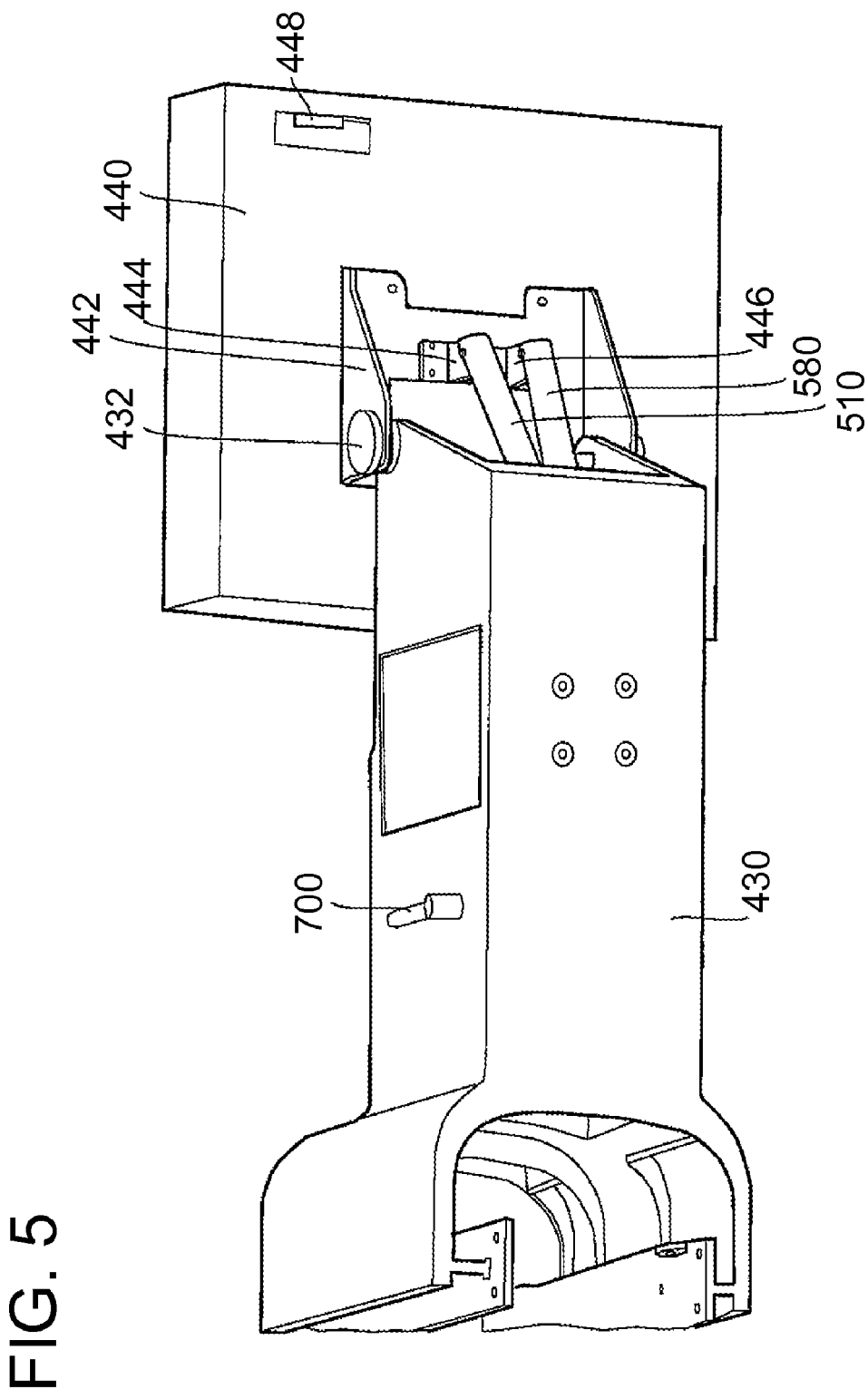
FIG. 5 is a view showing a constructional example of the angle adjusting mechanism.
Figure 6:
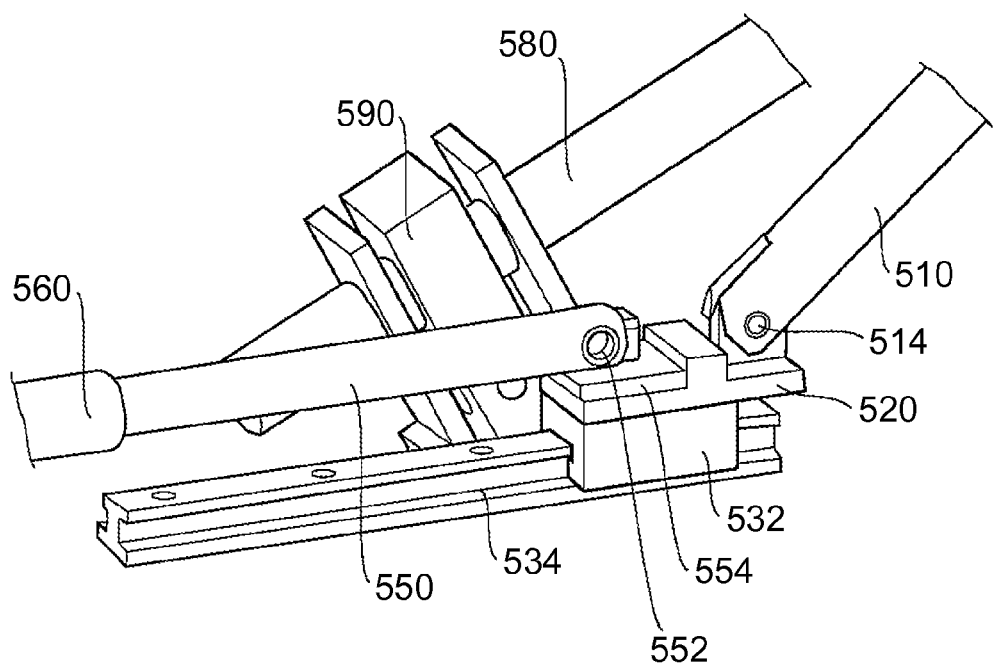
FIG. 6 is a view showing a constructional example of the angle adjusting mechanism.

FIGS. 3, 4 and 5 show a constructional example of the angle adjusting mechanism 500. FIGS. 3, 4 and 5 are vies of the angle adjusting mechanism 500 as seen sideways, from the front side, and from an obliquely downward position, respectively. FIG. 6 is an enlarged view of a part of the angle adjusting mechanism 500. The angle of the detector housing 440 is set at 90° (horizontal).

As shown in FIGS. 4 and 5, the bracket 442 is an inverted U-shaped member. The horizontal portion of the bracket 442 is fixed to the back surface of the detector housing 440 and tip ends of the vertical portions on both sides are connected to upper positions of the tip end of the arm 430 through horizontal shafts 432a and 432b, respectively. The horizontal shaft 432 and the bracket 442 are an example of the support mechanism defined in the present invention.

The angle adjusting mechanism 500 has a shaft 510. One end of the shaft 510 is connected through a pin 512 to a tip end of a support rod 444 suspending from the back surface of the detector housing. The support rod 444 is positioned ahead of the horizontal shafts 432a and 432b. The pin 512 is parallel to the horizontal shaft 432. The shaft 510 is an example of the shaft defined in the present invention.

An opposite end of the shaft 510 is connected to a shaft support 520 through a pin 514. The shaft support 520 underlies the horizontal shafts 432a and 432b. The pin 514 is parallel to the pin 512. The shaft support 520 is an example of the shaft support defined in the present invention.

The shaft support 520 is fixed onto a slider 532. The slider 532 is engaged with and movable along a rail 534. The rail 534 is fixed to the interior of the arm 430. The slider 532 and the rail 534 constitute a linear guide. The portion comprised of the slider 532 and the rail 534 is an example of the restriction mechanism defined in the present invention.

A tip end of a drive shaft 550 of a drive mechanism 540 is connected to the shaft support 520. As shown in FIG. 6, the tip end of the drive shaft 550 is put in contact from above with the shaft support 520 through an adaptor 554 which is connected to the drive shaft through a pin 552. The pin 552 is parallel to the pin 514. The shaft support 520 includes a horizontal surface with which a lower surface of the adaptor 554 is put in contact and a vertical surface with which a front end of the adaptor 554 is put in contact.

An opposite end side of the drive shaft 550 is positioned within a cylinder 560. In the interior of the cylinder 560 the power of a motor 570 acts on the drive shaft 550. The motor 570 is integral with the cylinder 560. With the power of the motor 570, the drive shaft 550 reciprocates rectilinearly in its longitudinal direction.

A base portion of the cylinder 560 is connected to a stud 564 through a pin 562. The pin 562 is parallel to the pin 552. The stud 564 is fixed to the interior of the arm 430. The drive mechanism 540 is supported at both ends thereof by both stud 564 and shaft support 520.

The drive mechanism 540 is pivotable about the pin 562. Consequently, a force based on a turning moment induced by the own weight of the drive mechanism 540 acts downwards on the contact portion between the adaptor 554 at the tip end of the drive shaft 550 and the shaft support 520.

In the drive mechanism 540, as a result of reciprocating motion of the drive shaft 550 caused by forward and reverse rotations of the motor 570, a lower end of the shaft 510 pinned to the shaft support 520 is allowed to reciprocate along the rail 534 and the detector housing 440 pinned to an upper end of the shaft 510 is allowed to pivot about the horizontal shaft 432, thereby adjusting the angle of the X-ray incidence surface.

The drive mechanism 540 is an example of the drive mechanism defined in the present invention. The motor 570 is an example of the motor defined in the present invention. The drive shaft 550 is an example of the drive shaft defined in the present invention. The portion comprised of the pin 562 and the stud 564 is an example of the second support mechanism defined in the present invention.

The angle adjusting mechanism 500 includes a brake shaft 580. One end of the brake shaft 580 is pinned to a tip end of a support rod 446 suspended from the back surface of the detector housing 440. The support rod 446 is positioned ahead of the horizontal shafts 432a and 432b. The pin is parallel to the horizontal shaft 432.

An opposite end side of the brake shaft 580 extends through a brake 590 which underlies the horizontal shaft 432. The brake 590 inhibits the passing of the brake shaft 580 where required. A lower end portion of the brake 590 is fixed to the interior of the arm 430 through a hinge. A shaft of the hinge is parallel to the horizontal shaft 432. As the brake 590 there is used, for example, an electromagnetic brake.

The brake 590 turns OFF and ON in interlock with operation and non-operation, respectively, of the motor 570. That is, during rotation of the motor 570, the brake 590 does not obstruct the passing of the brake shaft 580, while when the motor 570 is stopped, the brake 590 inhibits the passing of the brake shaft 580.

Therefore, while the drive mechanism 540 adjusts the angle of the detector housing 440, the brake 590 does not operate, and when the angle adjustment is over, the brake 590 turns ON and maintains the angle of the detector housing 440.

The portion comprised of the brake shaft 580 and the brake 590 is an example of the brake mechanism defined in the present invention. The brake shaft 580 is an example of the second shaft defined in the present invention. The brake 590 is an example of the brake defined in the present invention.

A lift mechanism 700 is annexed to the drive mechanism 540. The lift mechanism 700 is for lifting the drive mechanism 540 to pull a drive end of the drive mechanism apart from the object to be driven. The lifting operation is performed by applying force from below to induce an upward pivoting motion of the drive mechanism 540 about the pin 562.

The lifting of the drive mechanism 540 is done when adjusting the angle of the detector housing 440 manually. Since the drive end moves apart from the object to be driven as a result of the lifting operation, it becomes easy to effect the manual adjustment of the angle.

When the lifting operation is stopped, the drive mechanism 540 pivots downward and the drive end and the object to be driven again assume their contacted state. Thus, by operating the lift mechanism 700 manually, it is possible to switch from one to the other between contact and non-contact states of the drive end and the object to be driven. The lift mechanism 700 is an example of the switching mechanism defined in the present invention.

It is necessary that the manual adjustment of the angle of the detector housing 440 be performed with the brake 590 OFF. A brake operating switch 448 is disposed on the back surface of the detector housing 440. The switch 448 is an example of the brake operating means defined in the present invention.

Figure 7:
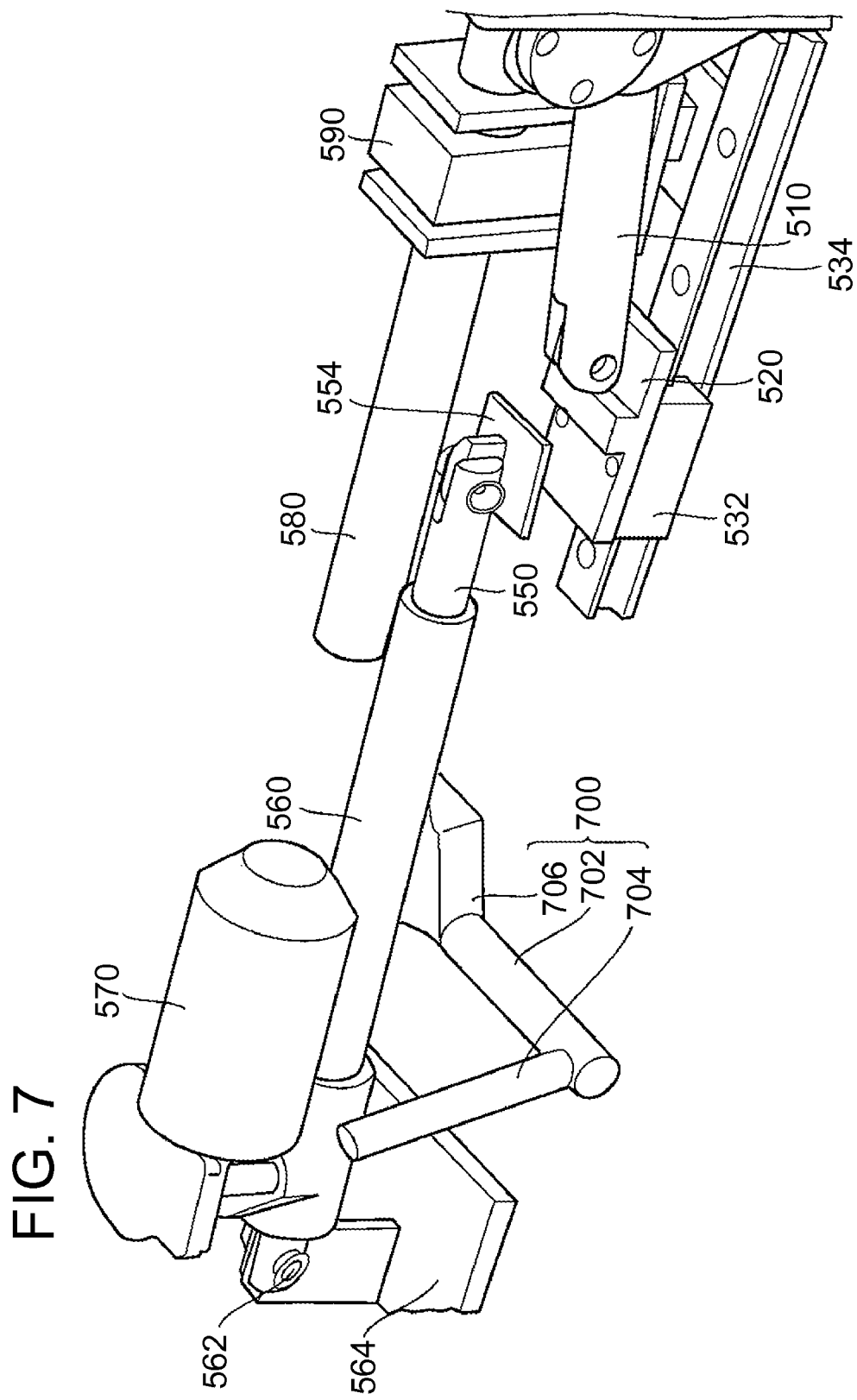
FIG. 7 is a view showing the structure of a lift mechanism.

FIG. 7 shows the structure of the lift mechanism 700. As shown in FIG. 7, the lift mechanism 700 comprises a shaft bar 702, as well as a vertical arm 704 and a lateral arm 706 both secured to the shaft bar 702. The shaft bar 702 is disposed under the drive mechanism 540 and in parallel with the horizontal shaft 432 and is attached to the arm 430 through a bearing (not shown). The vertical arm 704 is provided on one end of the shaft bar 702 at a position outside the arm 430, while the lateral arm 706 is provided so as to face forward at an intermediate position of the shaft bar 702 and just under the drive mechanism 540. The combination of the horizontal shaft bar 702 with the vertical arm 704 and the lateral arm 706 both provided on the shaft bar is an example of the lever defined in the present invention.

The vertical arm 704 is a handle for manual operation. By turning the vertical arm 704 to the left, the drive mechanism 504 can be lifted with the lateral arm 706. As a result of the lifting operation the adaptor 554 disposed at the tip end of the drive shaft 550 is pulled apart from the shaft support 520.

Figure 8:
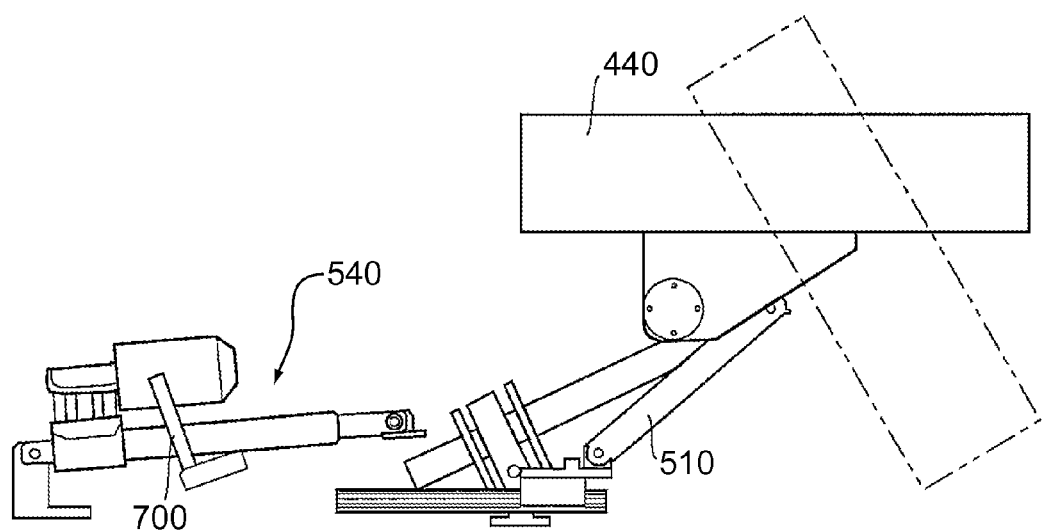
FIG. 8 is a view showing manual adjustment of the angle of a detector housing.
Figure 9:
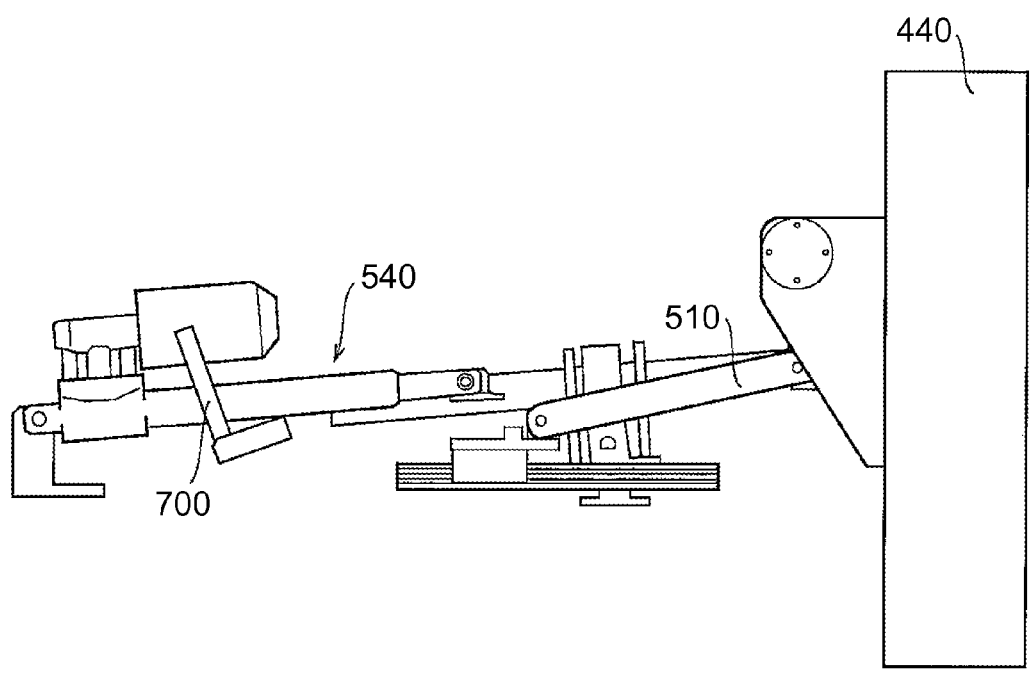
FIG. 9 is a view showing manual adjustment of the angle of the detector housing.
Figure 10:
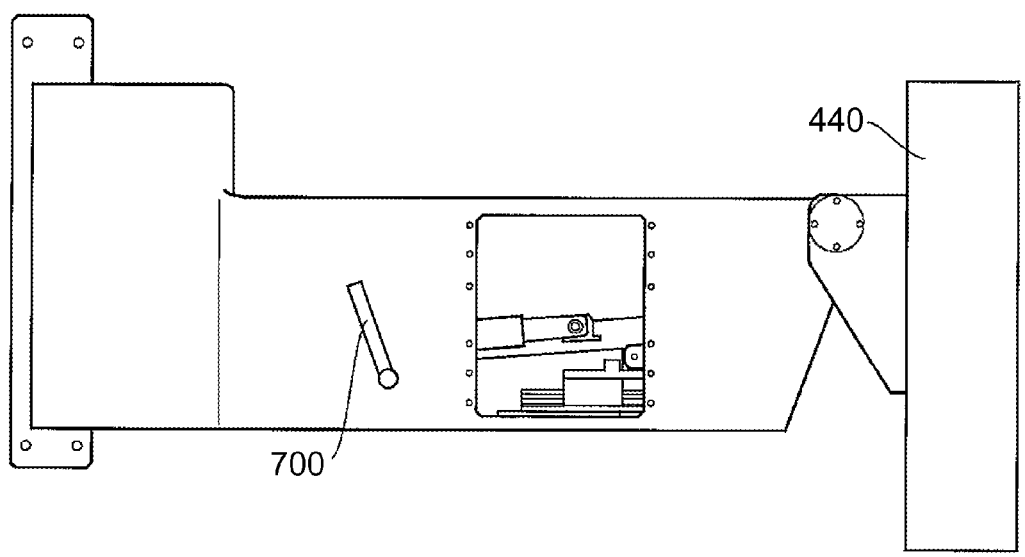
FIG. 10 is a view showing manual adjustment of the angle of the detector housing.

In this state, if the brake 590 is turned OFF by the switch 448, the maintenance of the angle of the detector housing 440 is released, so that it becomes possible to manually adjust the direction of the detector housing 440, as shown in FIGS. 8, 9 and 10. Then, if the brake 590 is actuated by the switch 448 in a desired state of inclination, the angle of the detector housing 440 is maintained.

What is claimed is:

1. An X-ray detecting device comprising:
   a detector housing comprising an X-ray incidence surface arranged in a changeable direction;
   a support mechanism configured to support the detector housing pivotably about a horizontal shaft parallel to the X-ray incidence surface;
   a shaft comprising a first end and an opposite second end, the first end coupled to the detector housing and second end adapted to perform a rectilinear motion to induce a pivotal motion of the detector housing;
   a drive mechanism comprising a drive end connected one of directly and indirectly to the second end of the shaft, the drive mechanism configured to induce the rectilinear motion of the second end of the shaft in a mutually connected state of the drive end and the second end of the shaft;
   a switching mechanism configured to switch between a state of connection and a state of non-connection of the second end of the shaft and the drive end;
   a brake mechanism configured to inhibit the pivotal motion of the detector housing; and a brake operating means configured to switch between a state of operation and a state of non-operation of the brake mechanism.

2. An X-ray detecting device according to claim 1, further comprising:
a shaft support joined to the second end of the shaft; and
a restriction mechanism configured to restrict a moving direction of the shaft support, wherein the drive end is connected to the shaft support.

3. An X-ray detecting device according to claim 1, wherein the support mechanism is configured to support a back surface of the detector housing by being apart from the horizontal shaft disposed on the back surface side of the detector housing.

4. An X-ray detecting device according to claim 3, wherein the support mechanism comprises a pair of parallel support arms spaced from each other in a direction of the horizontal shaft.

5. An X-ray detecting device according to claim 4, wherein the support arms are engaged with the horizontal shaft at respective ends on the side opposite to the detector housing.

6. An X-ray detecting device according to claim 2, wherein the restriction mechanism comprises:
a rectilinear rail; and
a slider adapted to move on the rail while carrying the shaft support thereon.

7. An X-ray detecting device according to claim 2, wherein the drive mechanism comprises:
a motor;
a drive shaft comprising a drive end, the drive shaft connected at the drive end to the shaft support and adapted to be driven by the motor to reciprocate in a rectilinear direction; and
a second support mechanism configured to support the motor and the drive shaft pivotably about a second horizontal shaft parallel to the horizontal shaft on a side corresponding to a second end of the drive shaft opposite to the drive end, to cause a force induced by a turning moment to act on a contact portion between the drive end and the shaft support.

8. An X-ray detecting device according to claim 7, wherein the switching mechanism comprises a lever configured to lift the drive mechanism to pull the drive end apart from the shaft support.

9. An X-ray detecting device according to claim 1, wherein the brake mechanism comprises:
a second shaft comprising a first end and an opposite second end, the first end connected through a pin parallel to the horizontal shaft to a position spaced apart from the horizontal shaft on a back side of the detector housing; and
a brake configured to inhibit movement of the second shaft.

10. An X-ray detecting device according to claim 9, wherein the brake comprises an electromagnetic brake.

11. An X-ray imaging apparatus comprising:
an X-ray irradiation device; and
an X-ray detecting device comprising:
a detector housing comprising an X-ray incidence surface arranged in a changeable direction;
a support mechanism configured to support the detector housing pivotably about a horizontal shaft parallel to the X-ray incidence surface;
a shaft comprising a first end and an opposite second end, the first end coupled to the detector housing and the second end adapted to perform a rectilinear motion to induce a pivotal motion of the detector housing;
a drive mechanism comprising a drive end connected one of directly and indirectly to the second end of the shaft, the drive mechanism configured to induce the rectilinear motion of the second end of the shaft in a mutually connected state of the drive end and the second end of the shaft;
a switching mechanism configured to switch between a state of connection and a state of non-connection of the second end of the shaft and the drive end;
a brake mechanism configured to inhibit the pivotal motion of the detector housing; and
a brake operating means configured to switch between a state of operation and a state of non-operation of the brake mechanism.

12. An X-ray imaging apparatus according to claim 11, further comprising:
a shaft support joined to the second end of the shaft; and
a restriction mechanism configured to restrict a moving direction of the shaft support, wherein the drive end is connected to the shaft support.

13. An X-ray imaging apparatus according to claim 11, wherein the support mechanism is configured to support a back surface of the detector housing by being apart from the horizontal shaft disposed on the back surface side of the detector housing.

14. An X-ray imaging apparatus according to claim 13, wherein the support mechanism comprises a pair of parallel support arms spaced from each other in a direction of the horizontal shaft.

15. An X-ray imaging apparatus according to claim 14, wherein the support arms are engaged with the horizontal shaft at respective ends on the side opposite to the detector housing.

16. An X-ray imaging apparatus according to claim 12, wherein the restriction mechanism comprises:
a rectilinear rail; and
a slider adapted to move on the rail while carrying the shaft support thereon.

17. An X-ray imaging apparatus according to claim 12, wherein the drive mechanism comprises:
a motor;
a drive shaft comprising a drive end, the drive shaft connected at the drive end to the shaft support and adapted to be driven by the motor to reciprocate in a rectilinear direction; and
a second support mechanism configured to support the motor and the drive shaft pivotably about a second horizontal shaft parallel to the horizontal shaft on a side corresponding to a second end of the drive shaft opposite to the drive end, to cause a force induced by a turning moment to act on a contact portion between the drive end and the shaft support.

18. An X-ray imaging apparatus according to claim 17, wherein the switching mechanism comprises a lever configured to lift the drive mechanism to pull the drive end apart from the shaft support.

19. An X-ray imaging apparatus according to claim 11, wherein the brake mechanism comprises:
a second shaft comprising a first end and an opposite second end, the first end connected through a pin parallel to the horizontal shaft to a position spaced apart from the horizontal shaft on a back side of the detector housing; and
a brake configured to inhibit movement of the second shaft.

20. An X-ray imaging apparatus according to claim 19, wherein the brake comprises an electromagnetic brake.

* * * * *